(12) United States Patent
Thornton

(10) Patent No.: US 7,060,090 B2
(45) Date of Patent: Jun. 13, 2006

(54) STENT WITH INCREASED LONGITUDINAL FLEXIBILITY AND SCAFFOLDING

(75) Inventor: Ronan Thornton, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 14 days.

(21) Appl. No.: 10/685,328

(22) Filed: Oct. 15, 2003

(65) Prior Publication Data

US 2005/0085899 A1 Apr. 21, 2005

(51) Int. Cl.
*A61F 2/06* (2006.01)

(52) U.S. Cl. ..................... 623/1.15; 623/1.16
(58) Field of Classification Search ............... 623/1.15, 623/1.16, 1.17
See application file for complete search history.

(56) References Cited

U.S. PATENT DOCUMENTS

| | | | |
|---|---|---|---|
| 5,853,419 A * | 12/1998 | Imran | 623/1.15 |
| 6,033,433 A * | 3/2000 | Ehr et al. | 623/1.16 |
| 6,113,627 A | 9/2000 | Jang | |
| 6,123,721 A | 9/2000 | Jang | |
| 6,217,608 B1 * | 4/2001 | Penn et al. | 623/1.16 |
| 6,261,319 B1 | 7/2001 | Kveen et al. | |
| 6,416,539 B1 | 7/2002 | Hassdenteufel | |
| 6,461,380 B1 * | 10/2002 | Cox | 623/1.17 |
| 6,478,816 B1 | 11/2002 | Kveen et al. | |
| 6,511,505 B1 * | 1/2003 | Cox et al. | 623/1.16 |
| 6,669,723 B1 * | 12/2003 | Killion et al. | 623/1.15 |

* cited by examiner

*Primary Examiner*—Bruce E. Snow
(74) *Attorney, Agent, or Firm*—Catherine C. Maresh

(57) ABSTRACT

The present invention relates to a stent manufactured from a thin-walled tube of surgical implant quality. The stent comprises a plurality of main circumferential rings, a plurality of longitudinal links and a plurality of intermediate circumferential rings. The main circumferential rings are longitudinally spaced apart along a longitudinal axis. Circumferential gaps are formed between adjacent main circumferential rings. The longitudinal links span the gaps and are attached to adjacent main circumferential rings. The intermediate circumferential rings fill in the circumferential gaps and are attached to the longitudinal links. The present invention thereby provides a stent with adequate radial strength to properly deploy, adequate scaffolding affect to properly support vessel walls and increased longitudinal flexibility to easily maneuver through tortuous vessels.

15 Claims, 4 Drawing Sheets

STENT WITH INCREASED LONGITUDINAL FLEXIBILITY AND SCAFFOLDING

BACKGROUND OF THE INVENTION

1. Field of the Invention

This invention relates generally to a novel stent design. More specifically, this invention relates to a stent having increased longitudinal flexibility with improved scaffolding affect.

2. Related Art

A stent is a prosthesis that is inserted into a body lumen and used, for example, for treating stenoses, strictures, and/or aneurysms therein. In the event of a stenosed vessel, the stent is expanded to widen and sometimes completely reopen a lumen. Once opened, the stent forms to the inner wall of the vessel, remains in place, and acts as a deterrent to restenosis. Additionally, in the event of an aneurysm or weakened vessel wall, stents are useful for providing support to and reinforcing the vessel wall.

To perform such functions, stents in the past have included many different structures. For example, previously disclosed stents include coiled stainless steel springs, helical wound springs, and generally serpentine configurations with continuous waves of generally sinusoidal character. Some of these stents self deploy when placed in the vessel, whereby stent expansion is primarily achieved by removing a restraint mechanism holding the stent in a constricted state. Other types of stents rely on alternate means to deploy, for example, use of a balloon catheter system, whereby balloon dilation expands and deploys the stent.

One of the major complications associated with using stents has been thrombosis. The complication is caused by clotting in the vicinity of the stent and is associated with high morbidity and mortality. It has been shown that the better the stent apposition against the vessel wall and the larger the lumen the less likely that this complication will occur. A further complication associated with stents is restenosis. This complication is caused by build up of plaque on the vessel's inner wall after the stent is in place. Accordingly, it is important that the stent cover the lesion not leaving any significant gaps by which restenosis may occur. It is also important that the stent adhere to the inner wall of the vessel as much as possible.

Accordingly, when a stent deploys in a restricted vessel, adequate radial strength is required to overcome the strictures and ensure apposition of the stent to the vessel wall. Radial strength is a force produced by the stent acting at all points on the vessel wall in an outwardly direction perpendicular to the vessel wall. Stents are designed with circumferential rings to provide most of the radial strength needed to overcome radial forces pushing inwardly against the stent as the stent expands. Stents also include longitudinal links that primarily act to attach longitudinally adjacent circumferential rings, but also add radial strength and stent stability. Once the stent is fully deployed, in addition to providing adequate radial strength, the stent must provide adequate vessel wall coverage, hereinafter referred to as scaffolding affect. Scaffolding affect is defined as the amount of area of the vessel wall covered by the stent, once the stent is fully deployed. The circumferential rings and longitudinal links connecting the circumferential rings have traditionally provided the needed scaffolding affect.

Further, to meet the demands of adequate radial strength and scaffolding affect, conventional stents have been designed with circumferential rings manufactured with adequate ring width, which were then continuously connected at each peak and trough by longitudinal links. However, such conventional stents suffer from predilation stent longitudinal rigidity. Predilation stent longitudinal rigidity is a resistance to movement and decreased flexibility of the stent along the stent's longitudinal axis. Accordingly, predilation longitudinal stent rigidity makes it much harder and oftentimes even impossible to thread the stent through long tortuous vessels and past constrictions and lesions.

Past attempts have been made to overcome predilation stent longitudinal rigidity. Such attempts have included designs with decreased ring width, often referred to as decreased wire gauge, which resulted in increased longitudinal flexibility but decreased radial strength. These conventional designs have resulted in inadequate stent apposition and/or inadequate vessel wall support. Additionally, past attempts to increase longitudinal flexibility have included designs where longitudinal links are not attached to each peak and trough of the circumferential ring. Thus, only some of the peaks and troughs of adjacent circumferential rings are connected by longitudinal links. This increases longitudinal flexibility but decreases the scaffolding affect of the stent. The decreased scaffolding affect creates areas where the vessel wall is not adequately covered by the stent, which may lead to thrombosis and/or restenosis.

Accordingly, there arises the need for a stent, which provides adequate radial strength, scaffolding affect and longitudinal flexibility. It is among the objects of the present invention to provide a stent that overcomes the foregoing shortcomings and meets the needs discussed above.

SUMMARY OF THE INVENTION

To achieve the foregoing and other objects, and in accordance with the purposes of the present invention as embodied and broadly described herein, the present invention comprises a generally hollow, tubular, wire mesh stent having a proximal end and a distal end. A longitudinal axis runs through the stent in a proximal to distal direction and a transverse axis runs in a radial direction.

Further, the stent comprises a plurality of main circumferential rings, a plurality of longitudinal links, and a plurality of intermediate circumferential rings. Each main circumferential ring forms a continuous outer circumference of the stent and is longitudinally spaced apart from the other main circumferential rings along the longitudinal axis from the proximal end to the distal end of the stent. Because the main circumferential rings are spaced apart, there is formed a plurality of circumferential regions in the stent void of the main circumferential rings, which are referred to herein as circumferential gaps.

The main circumferential rings are, for example, in the general shape of a sinusoidal wave. Accordingly, each main circumferential ring comprises a plurality of peaks, a plurality of troughs, a band length, and a mid band region. The band length is measured longitudinally along the longitudinal axis from a peak to a trough. The band length of the main circumferential ring is preferably larger than a band length for the intermedial circumferential ring (discussed below). Additionally, the main circumferential ring comprises a ring width. The ring width is a measure of a width of the wire comprising the main circumferential ring in a longitudinal direction. The main circumferential ring width is preferably larger than an intermediate circumferential ring width (discussed below).

The longitudinal links are also located around the outer circumference of the stent and span the plurality of circumferential gaps in the stent that are void of the main circumferential rings. The longitudinal links run generally parallel to the longitudinal axis, and extend between adjacent main circumferential rings. Each longitudinal link has a proximal end and a distal end. The longitudinal links may include a bend region or may simply be straight. The bend region is generally near the longitudinal middle of the longitudinal link and comprises a bend in the longitudinal link.

The longitudinal links are intermittently spaced circumferentially around the stent. Additionally, from one circumferential gap to the next longitudinally, the longitudinal links are staggered circumferentially. The longitudinal links may be unevenly intermittently spaced circumferentially at different longitudinal locations along the stent. For example, near the longitudinal middle of the stent, there may be fewer longitudinal links spaced around the stent circumference than near the stent ends. This creates larger circumferential distances between the longitudinal links.

The proximal and distal ends of the longitudinal links attach to the main circumferential rings. The longitudinal links may, for example, attach to the main circumferential rings in the mid band region of the main circumferential rings. Alternatively, the longitudinal links may attach to a peak or a trough of the main circumferential rings. Because the longitudinal links are intermittently spaced circumferentially, the longitudinal links are not attached to each and every peak, trough, or mid band region of the main circumferential rings.

Further, because the longitudinal links span the circumferential gaps between the main circumferential rings, they fill in part of the circumferential gaps created between the main circumferential rings. Along the stent where fewer longitudinal links are used circumferentially, a smaller area of the circumferential gaps is filled in. Accordingly, circumferential gaps remain along the longitudinal axis of the stent.

A plurality of intermediate circumferential rings are also positioned around the outer circumference of the stent, between the main circumferential rings and act to substantially fill in the remaining circumferential gaps. Accordingly, the intermediate circumferential rings span circumferentially the region between the longitudinal links and attach to the longitudinal links at preferably the bend region. In this way, the intermediate circumferential rings further fill in the void created by the gaps between the main circumferential rings.

The intermediate circumferential rings are preferably sinusoidal. Accordingly, the intermediate circumferential rings comprise a plurality of peaks, a plurality of troughs, and a band length. The intermediate circumferential ring band length is measured in the longitudinal direction along the longitudinal axis from a peak to a trough of the intermediate circumferential rings. Additionally, the intermediate circumferential ring comprises a ring width, which is a measure of a width of the intermediate circumferential ring wire in a longitudinal direction. The intermediate circumferential ring width is preferably smaller than that of the main circumferential ring width.

The stent of the present invention is thereby flexible because, for example, the longitudinal links are intermittently spaced in a staggered configuration along the stent's longitudinal axis. Additionally, the stent of the present invention provides adequate support to a vessel wall because, for example, the circumferential gaps created by the intermittent use of longitudinal links have been substantially filled in with intermediate circumferential rings. Further, the stent of the present invention, with, for example, a plurality of main circumferential rings, has adequate radial strength to properly deploy in a vessel. The stent of the present invention thereby provides flexibility to maneuver into place, adequate radial strength to properly deploy against a vessel wall, and adequate scaffolding affect to sufficiently cover a vessel wall once in place.

BRIEF DESCRIPTION OF THE DRAWINGS/FIGURES

DETAILED DESCRIPTION OF THE INVENTION

The foregoing and other features and advantages of the invention will be apparent from the following, more detailed description of the preferred embodiment of the invention, as illustrated with reference to FIGS. 1-4. While specific embodiments are discussed in detail, it should be understood that this is done for illustrative purposes only. A person skilled in the art will recognize that other embodiments can be used without departing from the spirit and scope of the invention.

Figure 1:
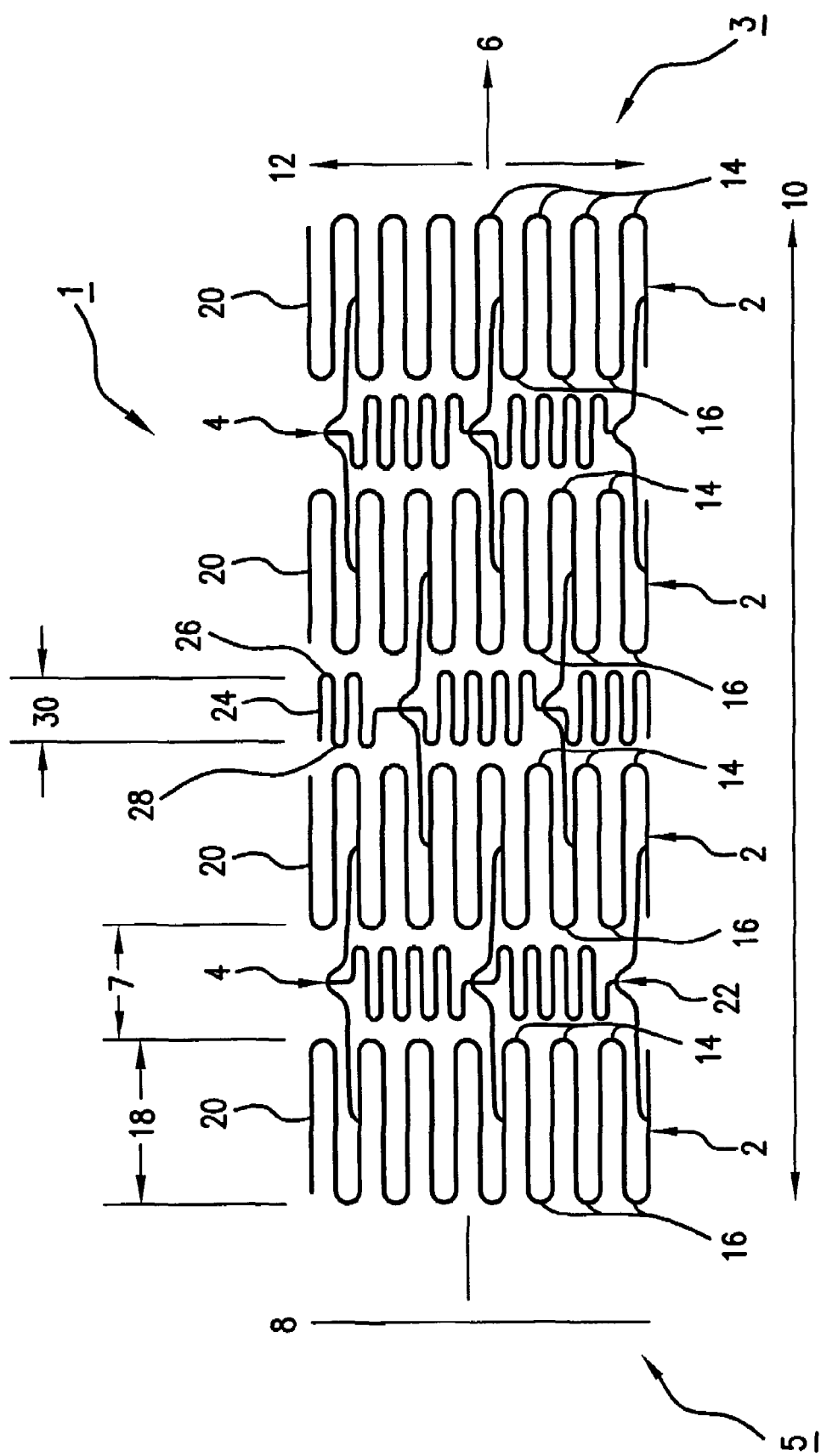
FIG. 1 is a top view of a stent of the present invention, showing main circumferential rings connected with an array of intermittent, circumferentially staggered longitudinal links, with intermediate circumferential rings attached to the longitudinal links.

FIG. 1 shows a top view of a stent 1, which has been cut and laid open for illustrative purposes. In its unaltered state, stent 1 is generally hollow and cylindrical in shape (not shown). Stent 1 has a proximal end 3 and a distal end 5. Additionally, stent 1 has a longitudinal axis 6 and a transverse axis 12. Further, stent 1 has a horizontal length 10 measured along longitudinal axis 6 from proximal end 3 to distal end 5, and a circumference 8 measured around the stent circumference.

Stent 1 comprises a plurality of main circumferential rings 2. The main circumferential rings 2 are longitudinally spaced apart along longitudinal axis 6. The main circumferential rings 2 are in the shape, for example, of a sinusoid. Each main circumferential ring 2 comprises a plurality of peaks 14 and troughs 16. The proximal end of the sinusoid has been arbitrarily labeled peak and the distal end of the sinusoid has been arbitrarily labeled trough. It would be understood by one of ordinary skill in the art that peaks 14 and troughs 16 have been labeled for illustrative purposes and ease of understanding and that the terms may be switched.

Additionally, each main circumferential ring 2 comprises a band length 18. The band length 18 is measured along longitudinal axis 6 from the peaks 14 of each sinusoid to the troughs 16 of each sinusoid. The band length 18 of each main circumferential ring 2 is consistent around circumference 8 throughout stent 1, and each main circumferential ring 2 has the same band length 18 as the other main circumferential rings 2. Additionally, the frequency of the sinusoid is constant around the circumference 8 and among the main circumferential rings 2. It would be understood by one of ordinary skill in the art that band length 18 may differ around circumference 8 or from one main circumferential ring to the next and that the frequency of the main circumferential ring may vary around the circumference or from one main circumferential ring to the next.

Further, each main circumferential ring 2 comprises a mid band region 20. The mid band region 20 is the region of the main circumferential ring 2 that is approximately parallel to the longitudinal axis 6 between the peaks 14 and troughs 16 of each main circumferential ring 2.

The main circumferential rings 2 run continuously around stent circumference 8 and provide the primary radial strength for stent 1. As the main circumferential rings 2 are spaced apart longitudinally along the longitudinal axis 6, a plurality of circumferential gaps 7 are formed between adjacent main circumferential rings 2. The circumferential gaps 7 are defined by the circumferential region that is longitudinally between the troughs 16 and peaks 14 of adjacent main circumferential rings 2.

Additionally, the stent 1 comprises a plurality of longitudinal links 4. The longitudinal links 4 are positioned around the outer circumference of the stent 1 and preferably run generally parallel to longitudinal axis 6. Longitudinal links 4 span circumferential gaps 7 formed between the main circumferential rings 2. Longitudinal links 4 attach at their ends to adjacent main circumferential rings 2. Longitudinal links 4 are shown attached at the mid band region 20 of the main circumferential ring 2. It would be understood by one of ordinary skill in the art that longitudinal links 4 may attach to the peaks 14 and troughs 16 of main circumferential rings 2. It would also be understood by one of ordinary skill in the art that longitudinal links 4 need not run generally parallel to longitudinal axis 6.

Longitudinal links 4 preferably have a bend region 22 that is generally longitudinally midway between the ends of the longitudinal links 4 and where, for example, the intermediate circumferential rings (discussed below) attach to longitudinal links 4. Again, it would be understood by one having ordinary skill in the art that longitudinal links 4 may be straight or any other geometric configuration. Additionally, longitudinal links 4 may vary in horizontal length and therefore either shorten or lengthen circumferential gap 7.

Stent 1 further comprises a plurality of intermediate circumferential rings 24. Intermediate circumferential rings 24 are located longitudinally between adjacent main circumferential rings 2 and substantially fill in the area in circumferential gaps 7.

Intermediate circumferential rings 24 are positioned around circumference 8 of stent 1. In this configuration, intermediate circumferential rings 24 are circumferentially located between longitudinal links 4 and attach thereto. Intermediate circumferential rings 24 attach to longitudinal links 4 in bend region 22. This embodiment shows longitudinal links 4 evenly spaced circumferentially along longitudinal axis 6. Longitudinal links 4 may be unevenly spaced circumferentially along longitudinal axis 4. Accordingly, for example, there may be less longitudinal links 4 in the longitudinal middle region of stent 1 than near proximal end 3 and distal end 5 of stent 1. This would add even greater longitudinal flexibility to the stent in the longitudinal middle region.

Intermediate circumferential rings 24 comprise a plurality of peaks 26 and a plurality of troughs 28. The longitudinal length along longitudinal axis 6 from the peaks 26 to the troughs 28 of each intermediate circumferential ring measures the intermediate circumferential ring band length 30. In this instance, band lengths 30 are consistent for each intermediate circumferential ring 24 around circumference 8 and the same among each intermediate circumferential ring 24. Intermediate circumferential band length 30 is different than main circumferential band length 18, and in this instance intermediate circumferential band length 30 is less than main circumferential band length 18.

If left unfilled, circumferential gaps 7 would leave significant amounts of the surface area of the inner wall of a vessel exposed when stent 1 is deployed against the vessel wall. Intermediate circumferential rings 24 act to fill in a significant part of circumferential gaps 7. In doing so, the scaffolding affect of stent 1 is increased. Accordingly, when stent 1 deploys against the inner wall of a vessel, a substantial part of the vessel's inner wall surface area is covered and supported by stent 1.

Figure 2:
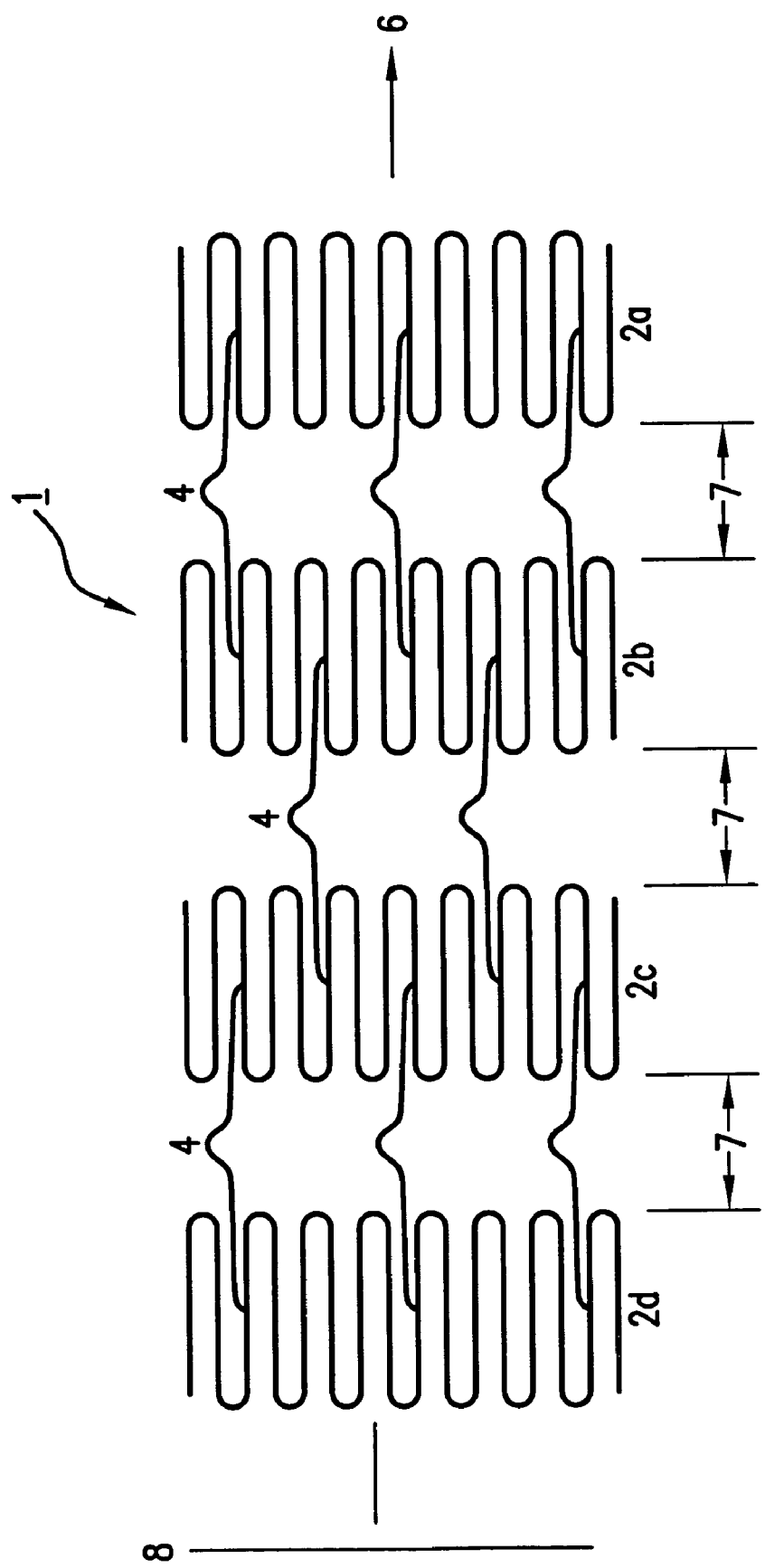
FIG. 2 is a top view of a stent of the present invention, showing main circumferential rings connected with an array of intermittent, circumferentially staggered longitudinal links, with intermediate circumferential rings removed.

FIG. 2 depicts a top view of stent 1, which has also been cut and laid open. For illustrative purposes, the intermediate circumferential rings 24 are not shown. Main circumferential rings 2 have been individually labeled 2a–2d for description purposes. Main circumferential rings 2a–2d and longitudinal links 4 are positioned around the outer circumference of stent 1 as described in FIG. 1. Longitudinal links 4 run in the longitudinal direction and are attached to adjacent main circumferential rings 2a–2d, also as described in FIG. 1. Longitudinal links 4 are intermittently spaced around the circumference 8 of stent 1. Longitudinal links 4 attach only to adjacent main circumferential rings. For example, longitudinal links 4 attach circumferential ring 2a to 2b, and 2b to 2c.

Additionally, longitudinal links 4 are staggered circumferentially along longitudinal axis 6. Accordingly, longitudinal links 4 that span circumferential gap 7 between main circumferential rings 2a and 2b do not attach to main circumferential ring 2b adjacent to where the longitudinal links 4 that span circumferential gap 7 between main circumferencial rings 2b and 2c attach to main circumferential ring 2b. This increases the longitudinal flexibility of stent 1. As there are fewer longitudinal links 4 circumferentially around the stent, stent rigidity is decreased and it is thereby easier to maneuver the stent through a tortuous path.

Figure 3:
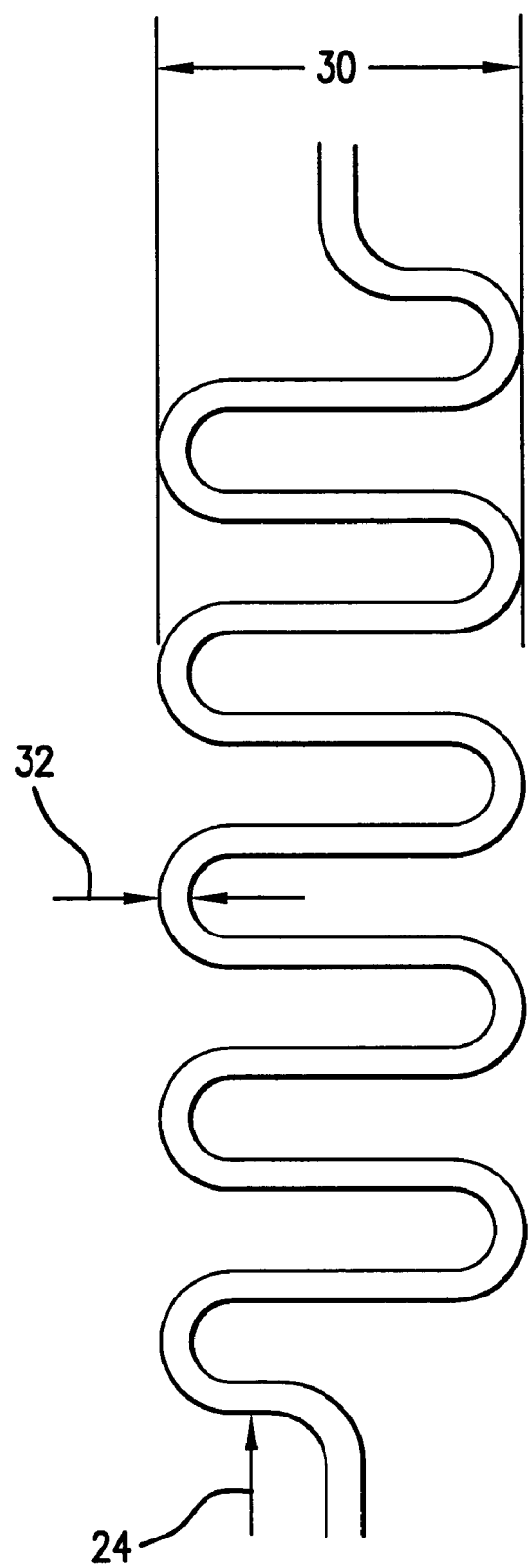
FIG. 3 is a top view of an intermediate circumferential ring showing, for example, intermediate circumferential ring band length and ring width.
Figure 4:
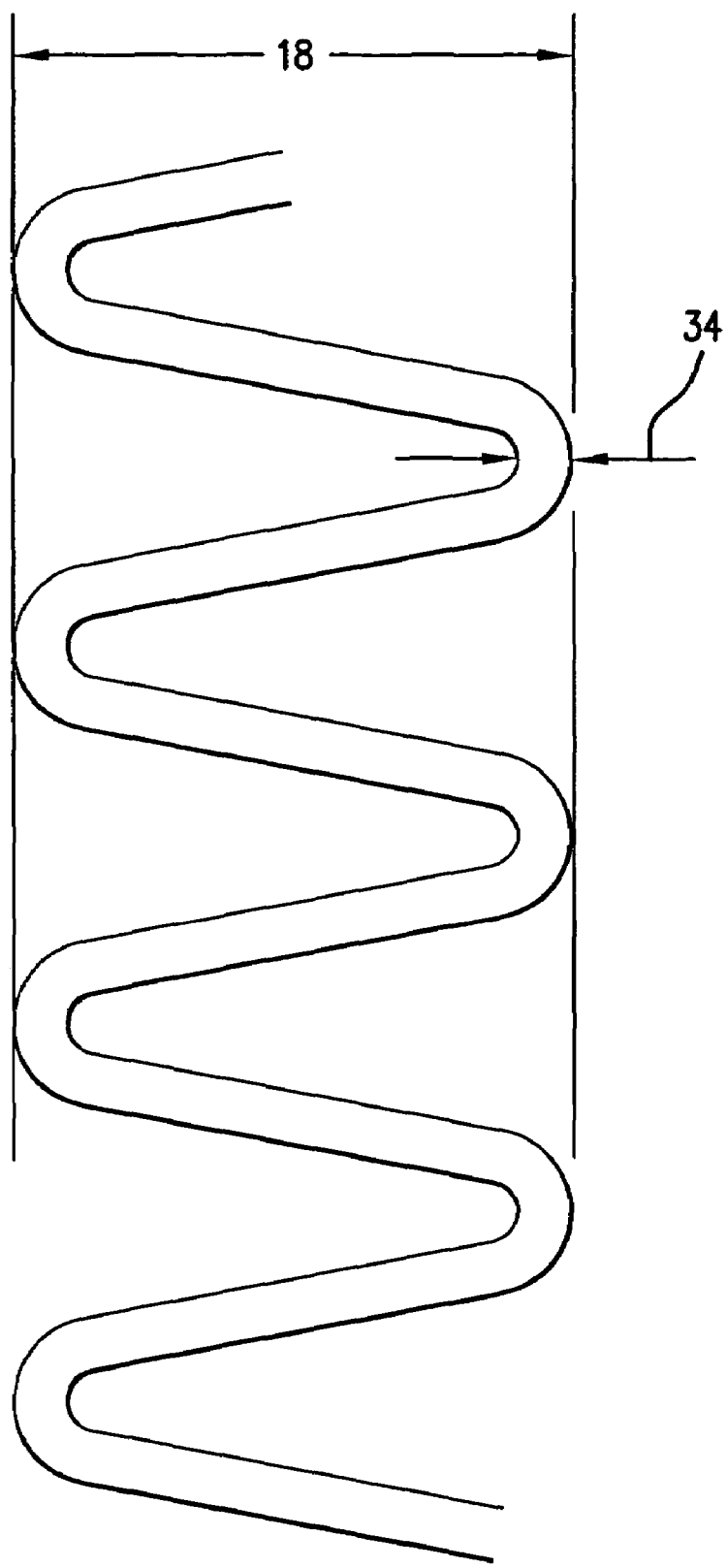
FIG. 4 is a top view of a main circumferential ring showing, for example, main circumferential ring band length and ring width.

FIG. 3 is a top view of an intermediate circumferential ring 24 as shown in FIG. 1. Intermediate circumferential ring 24 comprises band length 30 and a ring width 32. Band length 30 and ring width 32 are measured in a longitudinal direction. FIG. 4 is a top view of a main circumferential ring 2 as shown in FIG. 1. Main circumferential ring 2 comprises a band length 18 and a ring width 34. Band length 18 and ring width 34 are measured in a longitudinal direction.

As noted earlier, band length 30 and band length 18 are different, with band length 30 being smaller than band length 18. Additionally, ring width 32 is different than ring width 34, with ring width 32 being smaller than ring width 34 in this instance. Accordingly, in this instance main circumferential ring 2 is made of a heavier and stronger gauge material than intermediate circumferential ring 24.

As shown in the Figures and described above, the stent of the present invention is radially stronger and more flexible longitudinally while maintaining its scaffolding affect and thereby its ability to properly deploy and support the vessel wall. Fabrication of the stent described above can be accomplished in numerous ways.

One current method of fabrication is to stamp a sinusoidal wire configuration from a flat planar surface of surgical implant quality material and then to fuse its two opposite edges to create main circumferential ring 2. This process is repeated for the desired number of main circumferential rings. Additionally, longitudinal links 4 and intermediate circumferential rings 24 may also be stamped from a flat planar surface of surgical implant quality material, then longitudinal links 4 may be fused to main circumferntial rings 2 and intermediate circumferential rings 24 may be fused to longitudinal links 4.

A second method of fabrication is to first machine a flat ring from bar stock stainless steel type 316L or stamp a flat ring from a flat planar surface stainless steel type 316L. This process is repeated for the desired number of main circumferential rings. The segments are then tumbled in a media consisting of aluminum oxide, walnut shell and silicon carbide particles to produce a wire having a round cross section. The segments are then cleaned in alcohol and Synergy CCS™ cleaning solvent. The segments are annealed in a vacuum furnace on tungsten mandrels to make the metal easy to form.

The sinusoidal shape is formed in the segments to form main circumferential rings 2 by placing the segments on a form tool in contact with A2 tool steel caps and TanTung™ tool steel inserts. The main circumferential rings 2 are then placed on a tungsten mandrel and laser welded together with longitudinal links 4 and intermediate circumferential rings 24, which are also formed into the desired configuration in the process described above. Argon is used as a shielding gas for the welding.

The stent is then placed on a steel mandrel and swaged with tool steel dies to produce an elipto-rectangular cross section for the weld points. The stent is again annealed in a vacuum furnace on tungsten mandrels. Next, the stent is electropolished in a phosphoric and sulfuric acid based solution. A passive oxide layer is produced on the surface of the stent which is further enhanced by a 21% Nitric acid solution. Finally, the stent is cleaned in deionized water and alcohol.

Next, a preferred method of forming the stent of the present invention involves a laser cutting method. In the laser cutting method, a computer aided design (CAD) drawing of the stent is created. The CAD drawing is then used to generate a machine code, which in turn is used to drive a computer numerical control (CNC) laser system. Starting with a thin-walled seamless hollow cylinder of surgical implant quality of appropriate material, the CNC laser system cuts the stent in the appropriate pattern, by moving either the tube or the laser in a controlled manner.

Another method of forming the stent of the present invention includes a photolithographic method. In this method, a thin-walled seamless hollow cylinder of surgical implant quality of appropriate material is coated with photoresistant material. The coating is in the shape of the desired stent configuration. Next, the material of the hollow cylinder not coated with the photoresistant material is etched away leaving a stent with the desired configuration.

The width of individual elements within the stent may be varied as described above. For example, for a coronary stent, intermediate circumferential ring width 32 might be 0.06 mm and main circumferential ring width 34 might be 0.09 mm. The intermediate circumferential band length 30 might be, for example, 0.7 mm and the main circumferential band length 18 might be, for example, 1.1 mm. One of ordinary skill in the art would understand that the widths and lengths listed above might vary depending on where the stent is used in the body.

For example, a stent for a femoral artery will require a larger diameter and greater radial strength than that for a coronary artery. This can be achieved by increasing both the band length and the width of the individual elements. Such changes in stent dimensions can easily be achieved using the conventional manufacturing techniques discussed above. For example, the material for the stent may be selected from heavier gauge material, the machine code may be programmed such that the path of the laser beam results in a stent being cut with the desired dimensions, and the photoresistant material may be applied in such a way that results in the desired dimensions.

Accordingly, the specific examples of stent 1 described and discussed in the exemplary embodiments of the Figures are provided by way of example only and are not meant to limit the invention. Accordingly, while the invention has been particularly shown and described with reference to particular Figures thereof, it will be understood by those skilled in the art that various changes in form and details may be made therein without departing from the spirit and scope of the invention.

What is claimed is:

1. A stent comprising:
 a first main circumferential ring;
 a second main circumferential ring;
 a longitudinal link connecting said first main circumferential ring to said second main circumferential ring; and
 an intermediate circumferential ring disposed between said first main circumferential ring and said second main circumferential ring, wherein said intermediate circumferential ring includes a series of peaks, troughs and mid band regions between each peak and trough,
 wherein said intermediate circumferential ring is connected to said longitudinal link in at least one of the mid band regions of the intermediate circumferential ring, and
 wherein the longitudinal link is connected to only two main circumferential rings and only one intermediate circumferential ring.

2. The stent according to claim 1, wherein said longitudinal link attaches to said main circumferential rings at a mid band region.

3. The stent according to claim 1, wherein said longitudinal link includes a bend region.

4. The stent according to claim 3, wherein said intermediate circumferential ring attaches to said longitudinal link at said bend region.

5. A stent comprising:
 a plurality of main circumferential rings;
 a plurality of longitudinal links, wherein each longitudinal link connects adjacent main circumferential rings; and
 a plurality of intermediate circumferential rings, wherein each intermediate circumferential ring includes peaks, troughs, and a mid band region between each peak and trough,
 wherein each intermediate circumferential ring is attached to at least one longitudinal link at one of the mid band regions of the corresponding intermediate circumferential ring, and
 wherein the longitudinal link is connected to only two main circumferential rings and only one intermediate circumferential ring.

6. The stent according to claim 5, wherein said main circumferential rings comprise a ring width.

7. The stent according to claim 6, wherein said intermediate circumferential rings comprise a ring width.

8. The stent according to claim 5,
 wherein said intermediate circumferential rings comprise a band length that is different than said main circumferential ring band length.

9. The stent according to claim 8, wherein said longitudinal links are staggered circumferentially in a longitudinal direction.

10. The stent according to claim 9, wherein said intermediate circumferential rings extend between and attach to adjacent longitudinal links.

11. The stent according to claim 10, wherein said longitudinal links include a bend region.

12. The stent according to claim 11, wherein said intermediate circumferential rings attach to said longitudinal links at said bend region.

13. A stent comprising:
a first main circumferential ring;
a second main circumferential ring;
a longitudinal link connecting said first main circumferential ring to said second main circumferential ring; and
an intermediate circumferential ring disposed between said first main circumferential ring and said second main circumferential ring, wherein said intermediate circumferential ring includes a series of peaks, troughs and mid band regions between each peak and trough,
wherein said intermediate circumferential ring is connected to said longitudinal link in at least one of the mid band regions of the intermediate circumferential ring,
wherein said main circumferential ring width is different than said intermediate circumferential ring width.

14. The stent according to claim 13, wherein said main circumferential ring width is larger than said intermediate circumferential ring width.

15. The stent according to claim 13 wherein the longitudinal link is connected to only two main circumferential rings and only one intermediate circumferential ring.

* * * * *